US010180383B2

(12) United States Patent
Ndukaife et al.

(10) Patent No.: US 10,180,383 B2
(45) Date of Patent: Jan. 15, 2019

(54) SYSTEM AND METHOD FOR SENSING AND TRAPPING NANOPARTICLES WITH PLASMONIC NANOPORES

(71) Applicant: Purdue Research Foundation, West Lafayette, IN (US)

(72) Inventors: Justus C Ndukaife, West Lafayette, IN (US); Alexandra Boltasseva, West Lafayette, IN (US); Agbai Nnanna, Crown Point, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 15/476,868

(22) Filed: Mar. 31, 2017

(65) Prior Publication Data
US 2017/0284935 A1    Oct. 5, 2017

Related U.S. Application Data

(60) Provisional application No. 62/316,558, filed on Mar. 31, 2016.

(51) Int. Cl.
*G21K 1/00* (2006.01)
*G01N 15/00* (2006.01)
*G02B 5/00* (2006.01)
*B82Y 30/00* (2011.01)

(52) U.S. Cl.
CPC ............. *G01N 15/00* (2013.01); *G02B 5/008* (2013.01); *G21K 1/006* (2013.01); *B82Y 30/00* (2013.01)

(58) Field of Classification Search
CPC ........ G02B 5/008; G02B 1/002; G01N 15/00; G01N 15/10; G21K 1/006
See application file for complete search history.

(56) References Cited

U.S. PATENT DOCUMENTS

| | | | | |
|---|---|---|---|---|
| 7,696,473 | B2* | 4/2010 | Quidant | G21K 1/006 250/251 |
| 8,237,104 | B2* | 8/2012 | Neel | G02B 21/32 250/251 |
| 9,443,632 | B2* | 9/2016 | Wereley | G21K 1/006 |
| 2013/0182995 | A1* | 7/2013 | Erickson | B82Y 20/00 385/14 |
| 2015/0380120 | A1* | 12/2015 | Wereley | G21K 1/006 250/251 |

(Continued)

OTHER PUBLICATIONS

Ndukaife, Justus Chukwunonso, et al. "Photothermal heating enabled by plasmonic nanostructures for electrokinetic manipulation and sorting of particles." ACS nano 8.9 (2014): 9035-9043. (Year: 2014).*

(Continued)

*Primary Examiner* — Wyatt A Stoffa
(74) *Attorney, Agent, or Firm* — Purdue Research Foundation

(57) ABSTRACT

An apparatus for trapping and sensing nanoparticles using plasmonic nanopores, comprising a conductive transparent layer, a conductive film layer mounted to a substrate, the film layer comprising a plurality of nanopores for trapping nanoparticles contained in a fluid situated between the conductive transparent layer and the conductive film layer, and an electric field source connected between the transparent layer and the film layer.

15 Claims, 8 Drawing Sheets

(56) References Cited

U.S. PATENT DOCUMENTS

2016/0370316 A1* 12/2016 Ndukaife ............... G02B 5/008

OTHER PUBLICATIONS

Wang, Kai, et al. "Trapping and rotating nanoparticles using a plasmonic nano-tweezer with an integrated heat sink." Nature communications 2 (2011): 469. (Year: 2011).*
Ndukaife, Justus C., et al. "Long-range and rapid transport of individual nano-objects by a hybrid electrothermoplasmonic nanotweezer." Nature nanotechnology 11.1 (2016): 53 (Year: 2016).*
Yu, N., Flat optics with designer metasurfaces. Nat. Mater. 13, 139-50 (2014).
Kildishev, A., Planar photonics with metasurfaces. Science. 339, 1232009 (2013).
Yu, N., Light propagation with phase discontinuities: generalized laws of reflection and refraction. Science. 334, 333-7 (2011).
Ni, X., Broadband light bending with plasmonic nanoantennas. Science. 335, 427 (2012).
Yin, X., Photonic spin Hall effect at metasurfaces. Science. 339, 1405-7 (2013).
Pors, A., Gap plasmon-based metasurfaces for total control of reflected light. Sci. Rep. 3, 4184-4187 (2013).
Ma,G., Acoustic metasurface with hybrid resonances. Nat. Mater. 13, 873-878 (2014).
Xie, Y., Wavefront modulation and subwavelength diffractive acoustics with an acoustic metasurface. Nat. Commun. 5, 5553 (2014).
Aieta, F., Aberration-free ultrathin flat lenses and axicons at telecom wavelengths based on plasmonic metasurfaces. Nano Lett. 12, 4932-6 (2012).
Ni, X., Ultra-thin, planar, Babinet-inverted plasmonic metalenses. Light Sci. Appl. 2, e72 (2013).
Ni, X., Metasurface holograms for visible light. Nat. Commun. 4 (2013), doi:10.1038/ncomms3807.
Ni, X., An ultrathin invisibility skin cloak for visible light. Science. 349, 1310-4 (2015).
Balthasar, J., Ultracompact metasurface in-line polarimeter. Optica. 3, 42 (2016).
Boltasseva, A., Materials science. Low-loss plasmonic metamaterials. Science. 331, 290-291 (2011).
Khurgin, J., How to deal with the loss in plasmonics and metamaterials. Nat. Nanotechnol. 10, 2-6 (2015).
Lalanne, P., Blazed binary subwavelength gratings with efficiencies larger than those of conventional échelette gratings. Opt. Lett. 23, 1081 (1998).
Lalanne, P., Design and fabrication of blazed binary diffractive elements with sampling periods smaller than the structural cutoff. J. Opt. Soc. Am. A. 16, 1143 (1999).
Bomzon, Z., Space-variant Pancharatnam-Berry phase optical elements with computer-generated subwavelength gratings. Opt. Lett. 27, 1141 (2002).
Paniagua-Dominguez, R., Generalized Brewster-Kerker effect in dielectric metasurfaces. Nat. Commun., 1-9 (2016).
Lin, D., Dielectric gradient metasurface optical elements. Science. 345, 298-302 (2014).
West, P., All-dielectric subwavelength metasurface focusing lens. Opt. Express. 22, 26212-21 (2014).
Aieta, F., Applied optics. Multiwavelength achromatic metasurfaces by dispersive phase compensation. Science. 347, 1342-5 (2015).
Arbabi, A., Dielectric metasurfaces for complete control of phase and polarization with subwavelength spatial resolution and high transmission. Nat. Nanotechnol. 10, 937-943 (2015).
Khorasaninejad, M., Metalenses at visible wavelengths: Diffraction-limited focusing and subwavelength resolution imaging. Science. 352,1190-4 (2016).
Chong, K., Polarization-Independent Silicon Metadevices for Efficient Optical Wavefront Control. Nano Lett. 15, 5369-5374 (2015).
M. Khorasaninejad, W. Zhu, K. B. Crozier, Efficient polarization beam splitter pixels based on a dielectric metasurface. Optica. 2, 376 (2015).
Yang, Y., Dielectric Meta-Reflectarray for Broadband Linear Polarization Conversion and Optical Vortex Generation. Nano Lett. 14, 1394-1399 (2014).
Moerner, W., New directions in single-molecule imaging and analysis. Proc. Natl. Acad. Sci. U. S. A. 104,12596-602 (2007).
Belkin, M., Plasmonic Nanopores for Trapping, Controlling Displacement, and Sequencing of DNA. ACS Nano. 9, 10598-10611 (2015).
Benson, O., Assembly of hybrid photonic architectures from nanophotonic constituents. Nature. 480 (2011), pp. 193-199.
Whitesides, G., Self-assembly at all scales. Science. 295,2418-2421 (2002).
Glotzer, S., Self-assembly: From nanoscale to microscale colloids. AIChE J. 50,2978-2985 (2004).
Angelis, F., Breaking the diffusion limit with super-hydrophobic delivery of molecules to plasmonic nanofocusing SERS structures. Nat. Photonics. 5 (2011), pp. 682-687.
Nair, P., Performance limits of nanobiosensors. Appl. Phys. Lett. 88 (2006).
Squires, T., Making it stick: convection, reaction and diffusion in surface-based biosensors, doi:10.1038/nbt1388, 2008.
Sheehan, P., Detection Limits for Nanoscale Biosensors. Nano Lett. 5, 803-807 (2005).
Roxworthy, B., Plasmonic nanotweezers: strong influence of adhesion layer and nanostructure orientation on trapping performance. Opt. Express. 20, 9591 (2012).
Ghaemi, H., Extraordinary optical transmission through subwavelength hole arrays. Nature. 391, 667-669 (1998).
Popov, E., Theory of light transmission through subwavelength periodic hole arrays. Phys. Rev. B. 62, 16100-16108 (2000).
Liu, H., Microscopic theory of the extraordinary optical transmission. Nature. 452, 728-731 (2008).
Roxworthy, B., Toussaint, Understanding and controlling plasmon-induced convection. Nat. Commun. 5, 3173 (2014).
Ndukaife, J., Long-range and rapid transport of individual nano-objects by a hybrid electrothermoplasmonic nanotweezer. Nat Nanotechnol. 11, 53-9 (2016).
Yeh, S., Assembly of ordered colloidal aggregates by electric-field-induced fluid flow. Nature. 386 (1997), pp. 57-59.
Williams, S., Electrokinetic patterning of colloidal particles with optical landscapes. Lab Chip. 8, 1879-1882 (2008).
Santiago, J., A particle image velocimetry system for microfluidics. Exp. Fluids. 25 (1998), pp. 316-319.
Wereley, S., Advanced algorithms for microscale particle image velocimetry. AIAA J. 40 (2002), pp. 1047-1055.
Greffet, J., Coherent emission of light by thermal sources. Nature. 416,61-64 (2002).
Rousseau, E., Radiative heat transfer at the nanoscale. Nat. Photonics. 3,514-517 (2009).
Juan, M., Self-induced back-action optical trapping of dielectric nanoparticles. Nat. Phys. 5 (2009), pp. 915-919.

* cited by examiner

SYSTEM AND METHOD FOR SENSING AND TRAPPING NANOPARTICLES WITH PLASMONIC NANOPORES

CROSS-REFERENCE TO RELATED APPLICATIONS

The present patent application is related to and claims the priority benefit of U.S. Provisional Patent Application Ser. No. 62/316,558, filed Mar. 31, 2016, the contents of which is hereby incorporated by reference in its entirety into the present disclosure.

STATEMENT REGARDING GOVERNMENT FUNDING

This invention was made with government support under DMR-1120923 awarded by the National Science Foundation. The government has certain rights in the invention

TECHNICAL FIELD

The present application relates to particle sensing systems, and more specifically, to an apparatus and method for sensing nanoparticles in a fluid

BACKGROUND

Since the observation of Extraordinary Optical Transmission with apertures in a metal film by Thomas Ebessen and co-workers, a wide range of optoelectronic and optofluidic devices have been introduced. Applications have spanned from optical filters, imaging, to biomolecular detection. One of the most exciting applications of plasmonic nanopores or apertures is for enhanced trapping of nanometer scale objects, which cannot be addressed by conventional diffraction-limited laser tweezers. In such aperture-based tweezers, the trapped object plays an active role in the trapping process and further enhances the stability of the trap. However a key issue that remains is how to load the trap without relying on Brownian diffusion. All works on plasmonic aperture traps reported to date rely on waiting for random Brownian motion to deliver the particle to the aperture region, which is a very slow process. Moreover they also lack the ability to dynamically control the suspended particles. Therefore, improvements are needed in the field.

SUMMARY

According to one embodiment, an apparatus is provided, comprising a conductive transparent layer, a conductive film aperture layer mounted to a substrate, the aperture layer comprising a plurality of nanopores for trapping nanoparticles contained in a fluid situated between the transparent layer and the aperture layer, and an electric field source connected between the transparent layer and the aperture layer. A light source is provided and configured to illuminate the nanopores to induce a flow of the nanoparticles towards the nanopores.

BRIEF DESCRIPTION OF THE DRAWINGS

In the following description and drawings, identical reference numerals have been used, where possible, to designate identical features that are common to the drawings.

The attached drawings are for purposes of illustration and are not necessarily to scale.

DETAILED DESCRIPTION

In the following description, some aspects will be described in terms that would ordinarily be implemented as software programs. Those skilled in the art will readily recognize that the equivalent of such software can also be constructed in hardware, firmware, or micro-code. Because data-manipulation algorithms and systems are well known, the present description will be directed in particular to algorithms and systems forming part of, or cooperating more directly with, systems and methods described herein. Other aspects of such algorithms and systems, and hardware or software for producing and otherwise processing the signals involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

The present disclosure provides a plasmofluidic platform using nanoapertures in a metal film that may perform multiple functions: (1) fast and accurate delivery of nanoscale objects to the plasmonic hotspots in the plasmonic apertures where they can be trapped and fixed in place, (2) both high resolution and high throughput trapping of the nanoscale objects on a single lab-on-a-chip platform, (3) sensing of the nanoparticle trapped in the aperture, (4) rapid modulation of the environmental conditions, while sequentially transporting nanoparticles to the nanoaperture. These new desirable trapping functionalities have remained elusive until now and will expand the range of applicability of the aperture-based plasmonic tweezers in several fields including single molecule analysis, biomolecular sensing, imaging, on-chip nano-manufacturing and quantum nanophotonics. Furthermore, plasmonic apertures are promising for use as nanopores for single molecule analysis and sequencing of DNA.

Figure 1:
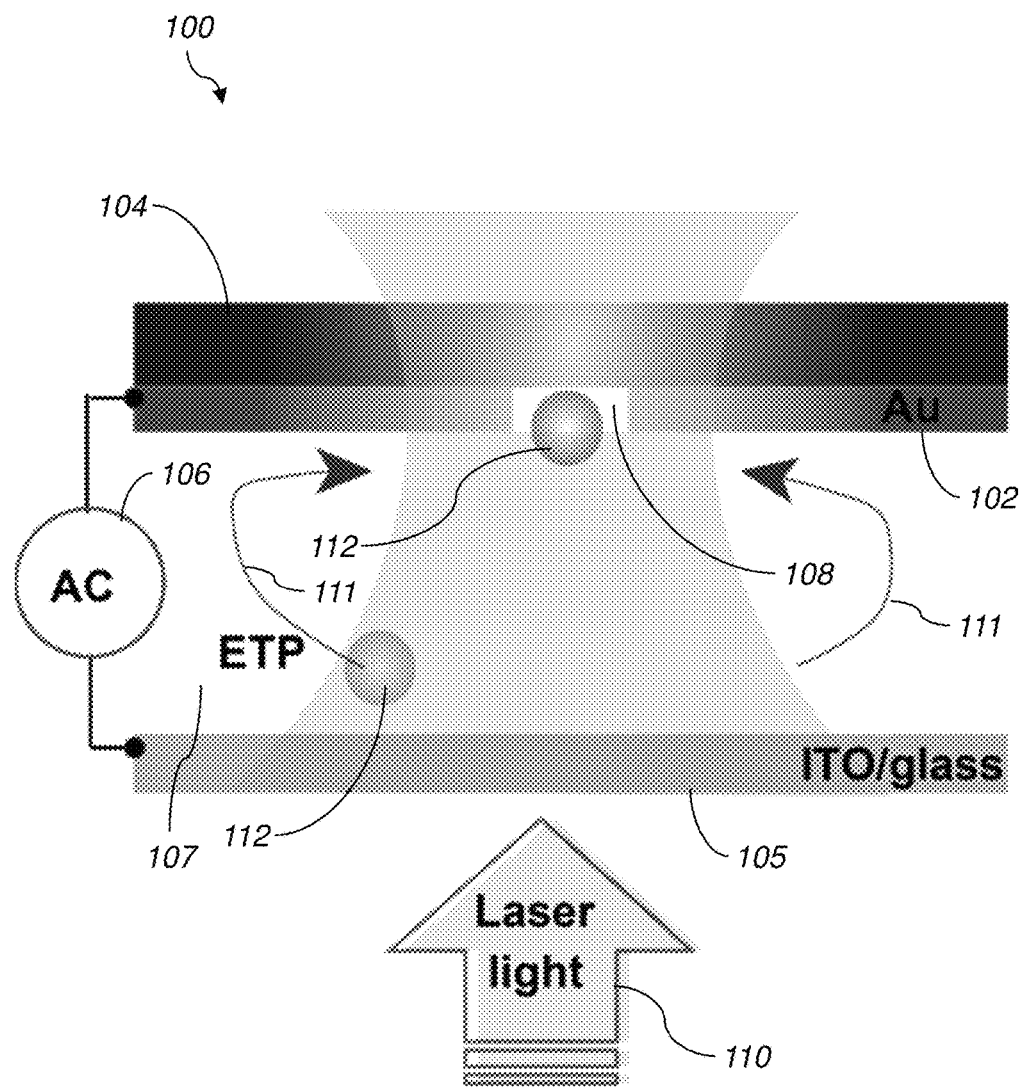
FIG. 1 is a diagram showing an apparatus for trapping nanoparticles with a plasmonic nanopore according to various aspects.

FIG. 1 shows an apparatus 100 for trapping nanoparticles with a plasmonic nanopores according to various aspects. The apparatus 100 may comprise an electrically conductive and optically reflective film aperture layer 102 mounted to a substrate 104, a conductive transparent layer 105, and an electric field source 106 connected between the aperture layer 102 and the transparent layer 105. The aperture layer 102 comprises a plurality of nanopores (or apertures) 108. The nanopores 108 have a diameter preferably in the range of 2 nm to 900 nm, although other larger or smaller ranges may also be used. The aperture layer 102 may be made from a conductive material, such as gold, silver, copper, titanium nitride, zirconium nitride, hafnium nitride, tantalum nitride and other plasmonic materials and have a thickness preferably in the range of 1 nm to 500 nm, although larger or smaller thicknesses may also be used. In the illustrated example, nanopores with a diameter of 500 nm are used and a 100 nm thick gold film layer is used. The transparent layer 105 may comprise any transparent conductive material, such as indium tin oxide (ITO), aluminum doped zinc oxide, thin layer of metal film on a substrate and the thickness of the relatively transparent layer on a substrate may range from 10 nm to 1000 nm. In certain embodiments, a bullseye grating may be included, either separately or as part of the transparent layer 105. The bullseye grating may comprise a plurality of focusing elements which align and focus the light source 110 to the nanopores 108. The bullseye grating surrounding the nanopore 108 can be on opposite sides of the metal film aperture layer 102 and used to both focus light into the central nanopore and/or outcouple light from the nanopore 108 to free space. In other embodiments, a metasurface lens which focuses the light source onto the nanopores 108 is provided, either separately or as part of the transparent layer 105. The electric field source 106 may comprise an alternating current (AC) source, a voltage source, or any electric field source suitable to create an electric field in the region between the aperture layer 102 and the transparent layer 105 when connected across the aperture layer 102 and the transparent layer 105. The electric field source preferably produces an electric field having a frequency in the range of 5 KHz-100 KHz and field strength in the range of 40,000-1,000,000 volts per meter. The field strength is preferably limited to be below the breakdown voltage of water (the voltage at which the water itself becomes conductive). A light source 110 may also be provided. The light source 110 may comprise a laser, a broadband light source directed through focusing and/or filtering elements, or other light source. It shall be understood that the light source 110 may comprise a single light source or a plurality of light sources.

In operation, the electric field source is applied between the aperture layer 102 and transparent layer 105 to generate an electric field between the aperture layer 102 and conductive layer 105. The light source 110 is directed through the transparent layer 105, resulting in illumination of the nanopore 108. The illumination of the nanopore 108 results in the excitation of localized surface plasmon resonance in the nanopore 108, which enhances the electromagnetic field near the rim of the nanopore 108. The enhanced electric field inside the nanopore 108 is used to trap nanoscale objects 112 contained in a fluid 107 that have been delivered to the nanopore 108. The objects 112 may comprise biomolecules or any other particles having nanoscale dimensions.

Figures 2A, 2B:
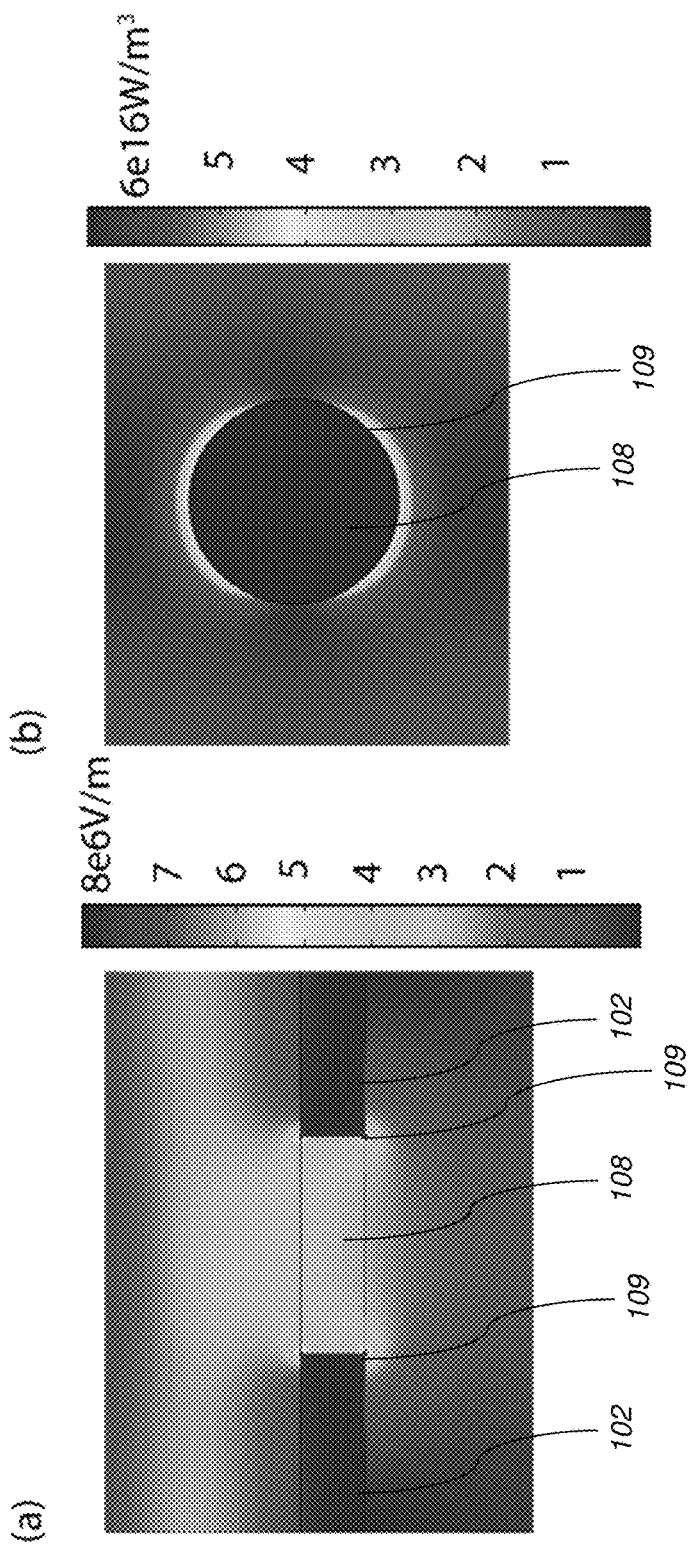
FIG. 2a is a side view image showing a simulated electric field in the vicinity of an illuminated nanohole according to various aspects.
FIG. 2b is top view image showing distribution of the electromagnetic power loss density near a nanohole according to various aspects.

FIG. 2a shows the simulated electric field distribution near the nanopore 108, where it is evident that strong localization and enhancement of the field occurs within the nanopore 108 and near the rims 109 of the nanopore 108. In order to deliver the suspended particle 112 to the nanopore where it will be trapped, a strong microfluidic flow is generated on-demand to deliver particles 112 to the nanopores 108. The mechanism to generate this on-demand fluidic motion is explained as follows. The absorption of light around the nanopore rims 109 results in energy dissipation in that region (near the rims 109). As shown in FIG. 2b, the electromagnetic power loss density is also increased near the rim 109 and this serves as a source of heat to increase the temperature. This in turn results in local heating of the region within and near the nanopore 108, which gives rise to a gradient in the temperature-dependent electrical conductivity and permittivity of the fluid 107. By applying an AC electric field under this condition, a strong body force is induced in the fluid 107 on-demand to enable fast and precise delivery of individual objects 112 to the plasmonic trapping sites (nanopores 108). This electrothermoplasmonic (ETP) flow (indicated by arrows 111) toward the nanopores 108 is significantly increased when the nanopore 108 is illuminated in comparison to prior art devices.

In one example of the disclosed apparatus 100, the velocity of the electrothermoplasmonic flow induced by illuminating the plasmonic nanopore 108 and applying an AC electric field using source 106 was measured using a technique called micro particle image velocimetry. For the experiment, the AC electric field applied was 80,000 V/m while the frequency was set to 50 KHz. Tracer particles comprising of fluorescent 300 nm diameter polystyrene beads were introduced to visualize the flow. These same particles were also used to demonstrate the trapping experiments. The illumination of the nanopores 108 in conjunction with the applied AC electric field resulted in the generation of strong electrothermoplasmonic flow of particles 112 within the fluid 107 toward the nanopores 108. The substantially increased flow was present when both the AC electric field and laser illumination of the nanopores are simultaneously present as enabled by the disclosed apparatus 100.

Figure 3:
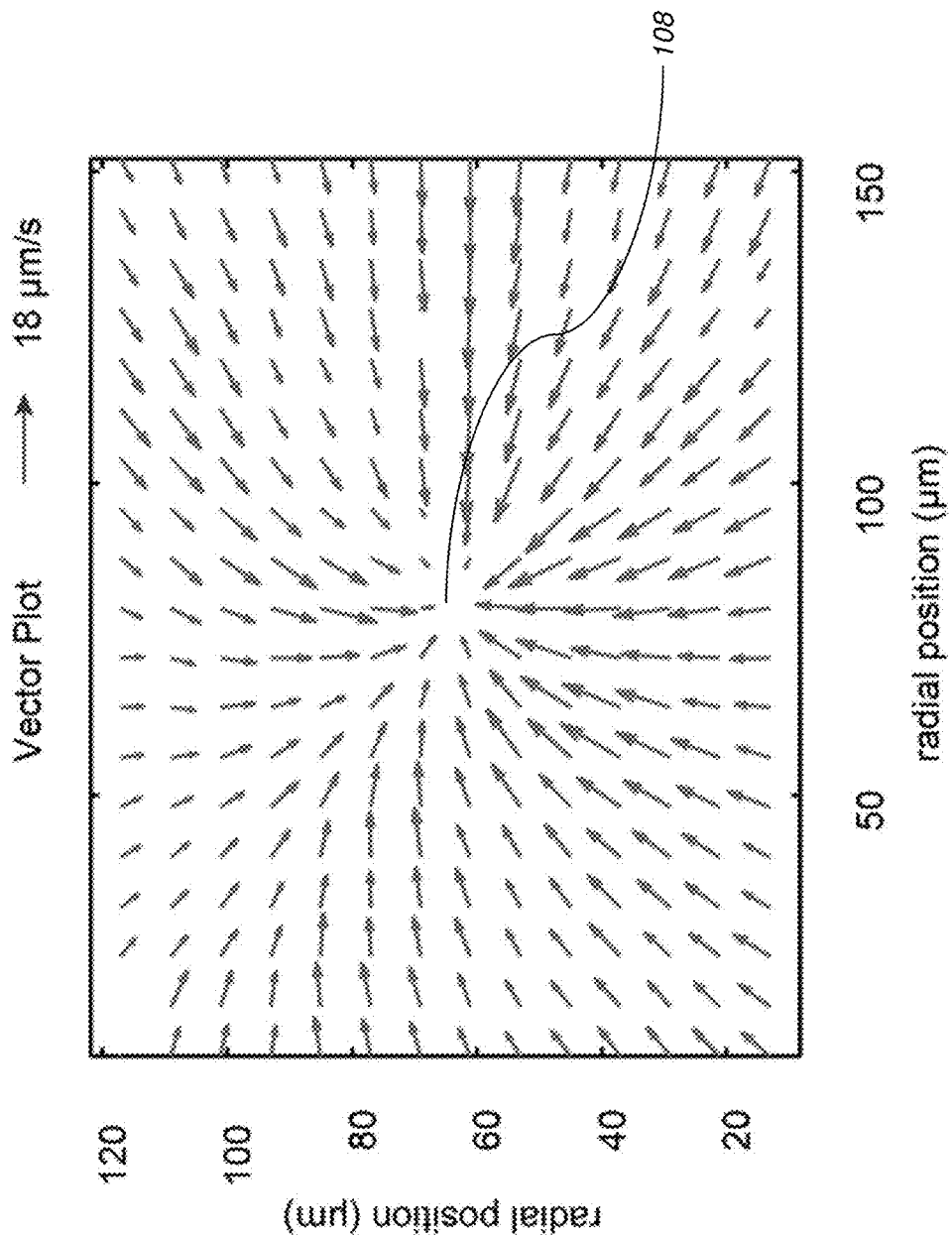
FIG. 3 is a diagram showing a radial velocity vector distribution when the nanoaperture is illuminated with an AC electric field applied according to various aspects.

The radial velocity vector depicted in FIG. 3 shows that the fluidic flow acts to transport the particles towards the illuminated nanopore 108 which is also the trapping site according to one embodiment. As shown in FIG. 3, the maximum radial velocity is about 15 μm/s. In comparison we found that the maximum velocity of the electrothermoplasmonic flow when the plasmonic nanopore 108 is illuminated is at least two times higher than when only the planar film section was illuminated. This is due to the fact that the plasmonic nanopore 108, when illuminated at the resonant wavelength, acts as an antenna to funnel light to its vicinity near the rims 109. This results in large power dissipation near the rim 109 of the nanopore 108. This result is particularly important and serves as a novel approach to detect when the beam of light source 110 is positioned on the nanopore 108, which is very useful, especially with near infrared illumination which is not visible.

Figure 4:
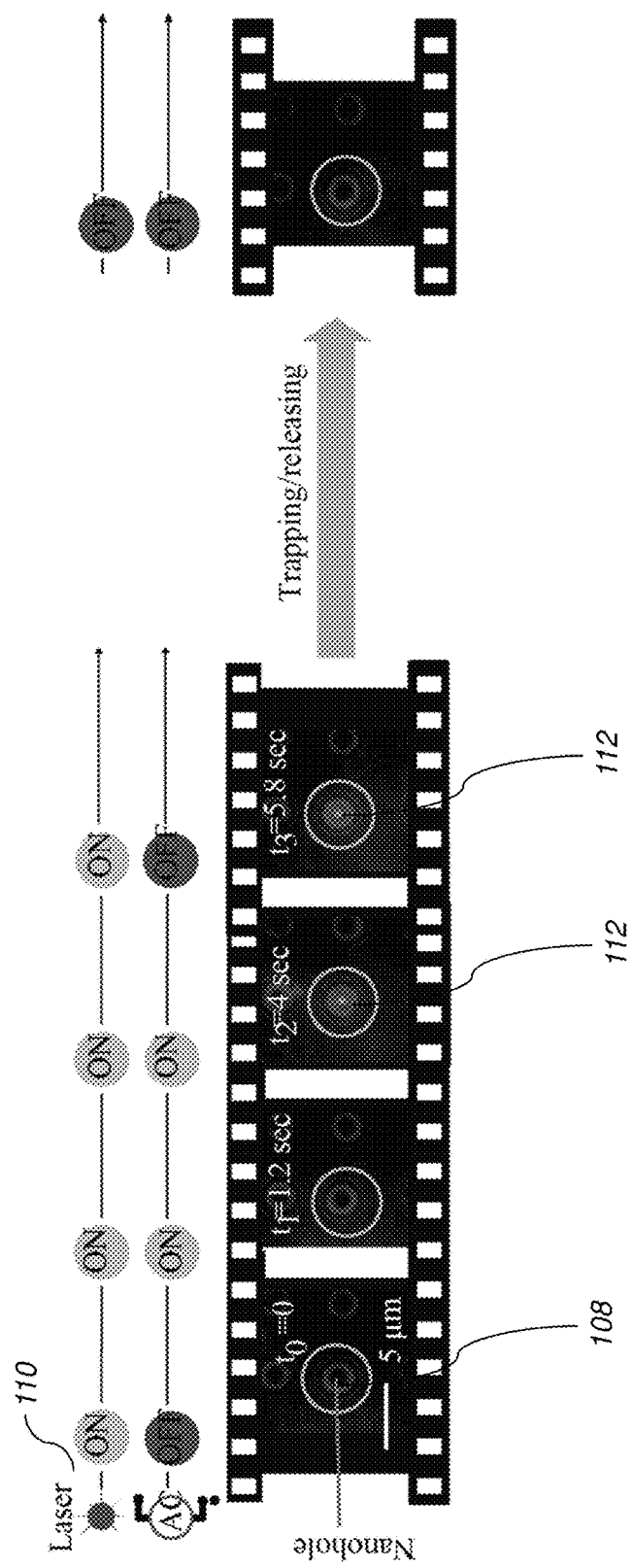
FIG. 4 is a diagram showing the sequence of capture, transport and trapping of a nanoparticle in the novel nanopore nanotweezer. The figure also shows how a trapped particle is released by turning off laser illumination according to various aspects.

In one example, trapping of nanoparticles using the plasmonic nanopore-based electrothermoplasmonic nanotweezer was performed by using 300 nm diameter fluorescent polystyrene beads. The experimental results are shown in FIG. 4. Initially, only laser illumination of the 500 nm nanopore was applied. Under this condition, the suspended particles 112 undergo Brownian diffusion and no net motion was observed. However when the AC electric field was also applied (using source 106), substantial electrothermoplasmonic flow is induced in the fluid 107. The flow captures suspended particles 112 and rapidly transports them towards the illuminated nanopores 108 where they are trapped within a few seconds. The trapped particles 112 remain trapped even after the AC field was turned off with the laser illumination still on. This is because the gradient force induced by the illuminated plasmonic nanopore 108 keeps the delivered particles 112 trapped in place.

In certain embodiments, the device 100 is implemented as a sensor. Sensing is achieved by monitoring the electrothermoplasmonic flow strength when the particle 112 has been delivered to the nanopore 108. Since the nanopore 108 is a region of high energy density, if a metallic particle is delivered to the nanopore 108, there will be strong light absorption and strong temperature gradient. As result the velocity of the electrothermoplasmonic flow will be higher in comparison with the case whereby a dielectric or less metallic nanoparticle 108 is trapped. Thus the device 100 may be used to discriminate between particles based on their material properties. Furthermore it may also be implemented as a single molecule analysis. Gold nanoparticles 112 may be functionalized to bind with certain analytes such as protein. The nanopores 108 are functionalized with an antibody for the target protein. Once the gold nanoparticle 112 that has bound with target protein is delivered to the nanopore 108, the protein on its surface will bind to the antibody in the nanopore 108. The electothermoplasmonic flow under this condition is recorded. Next the laser and AC field will be turned OFF. If the protein on the gold nanoparticle 112 has bound with its antibody in the nanopore 108, the gold nanoparticle 112 will still remain in the nanopore 108 even after the singles has been turned OFF. Next the laser and AC field are turned ON and the electrothermoplasmonic flow velocity is measured and compared with the previous case before both laser AC field where turned OFF. If the strength of the flow re the same, then bind between the protein on the gold nanoparticle and the antibody protein on in the nanopore has taken place. The biomolecular interaction can also be other biomolecules such as between DNA strands and virus and protein.

Figure 5:
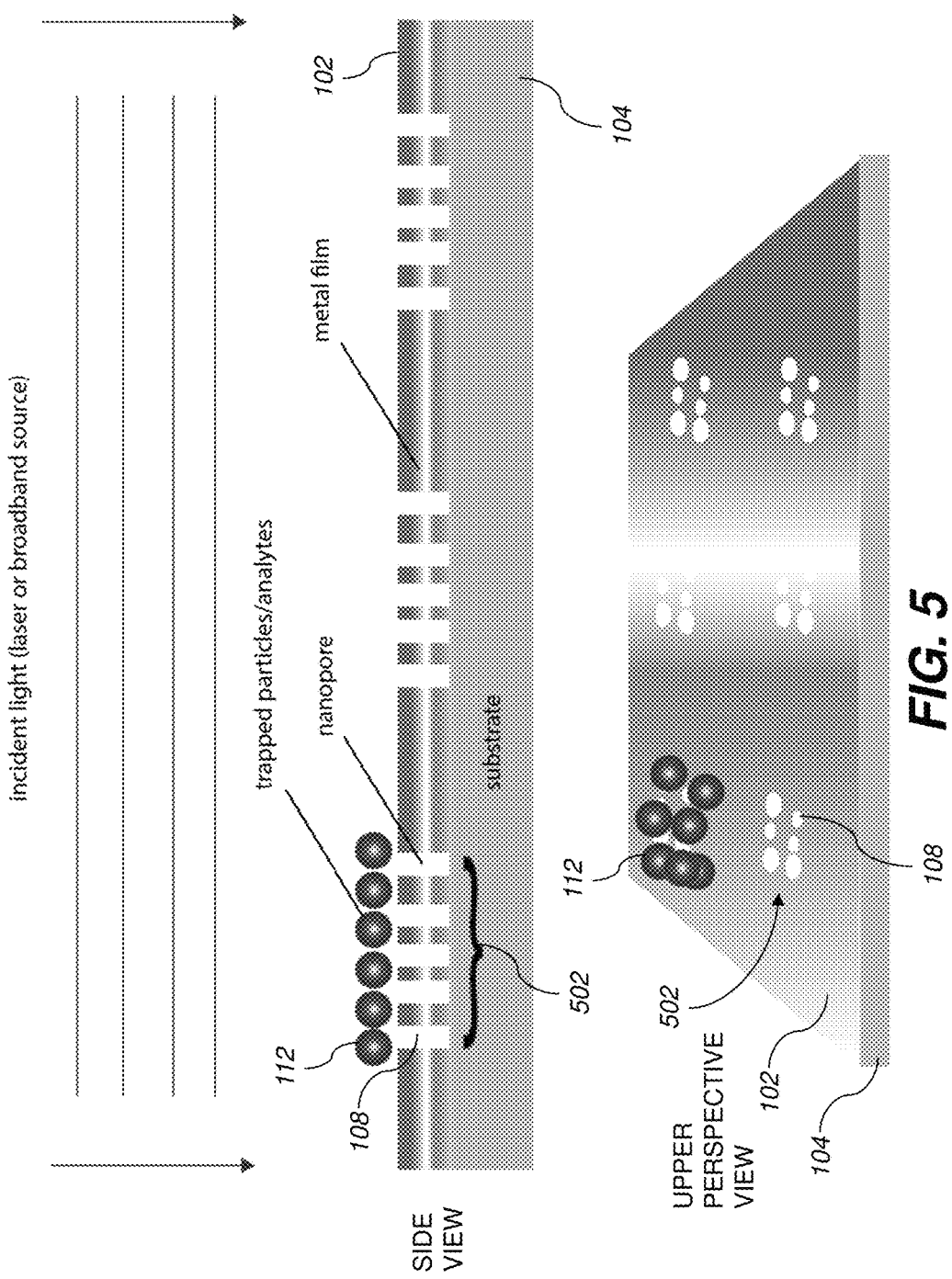
FIG. 5 is a diagram showing a nanoparticle trapping apparatus having random arrays of nanopores according to various aspects.

FIG. 5 shows a further embodiment having a random arrays 502 of nanopores 108 arranged at multiple locations on a substrate. An orderly arranged array of nanopores 108 can also be used. The array extends over several microns to several tens of microns. The arrays of nanopores 108 are arranged such that multiple arrays can be illuminated by a light source. The excitation of the array of nanopores 108 with light results in the generation of surface plasmon polaritons that give rise to strong absorption of the light and those sites serve as multiple trapping sites. An AC electric field is applied, causing multiple electrothermoplasmonic flows to be induced at the multiple sites where the arrays of nanopores 108 are present. Nanoparticles 112 are captured and rapidly delivered to these multiple sites where they are trapped. The arrays of nanopores 108 are functionalized to bind target analytes and after binding the change in the color of the light emerging from the nanopore arrays is correlated with the concentration of the analytes.

Figure 6:
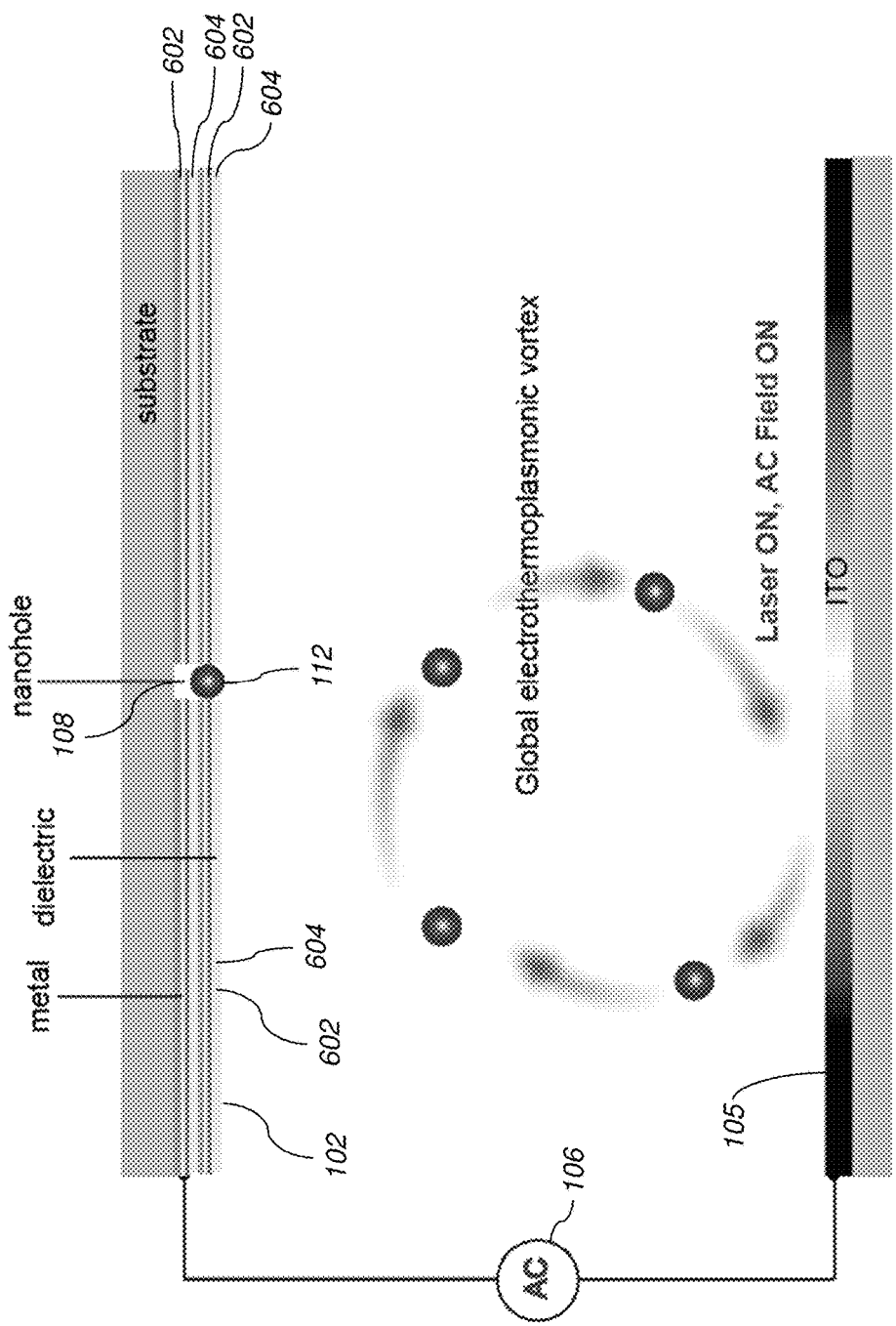
FIG. 6 is a diagram showing an embodiment having a film comprising alternating sections of metal dielectric composites.
Figure 7:
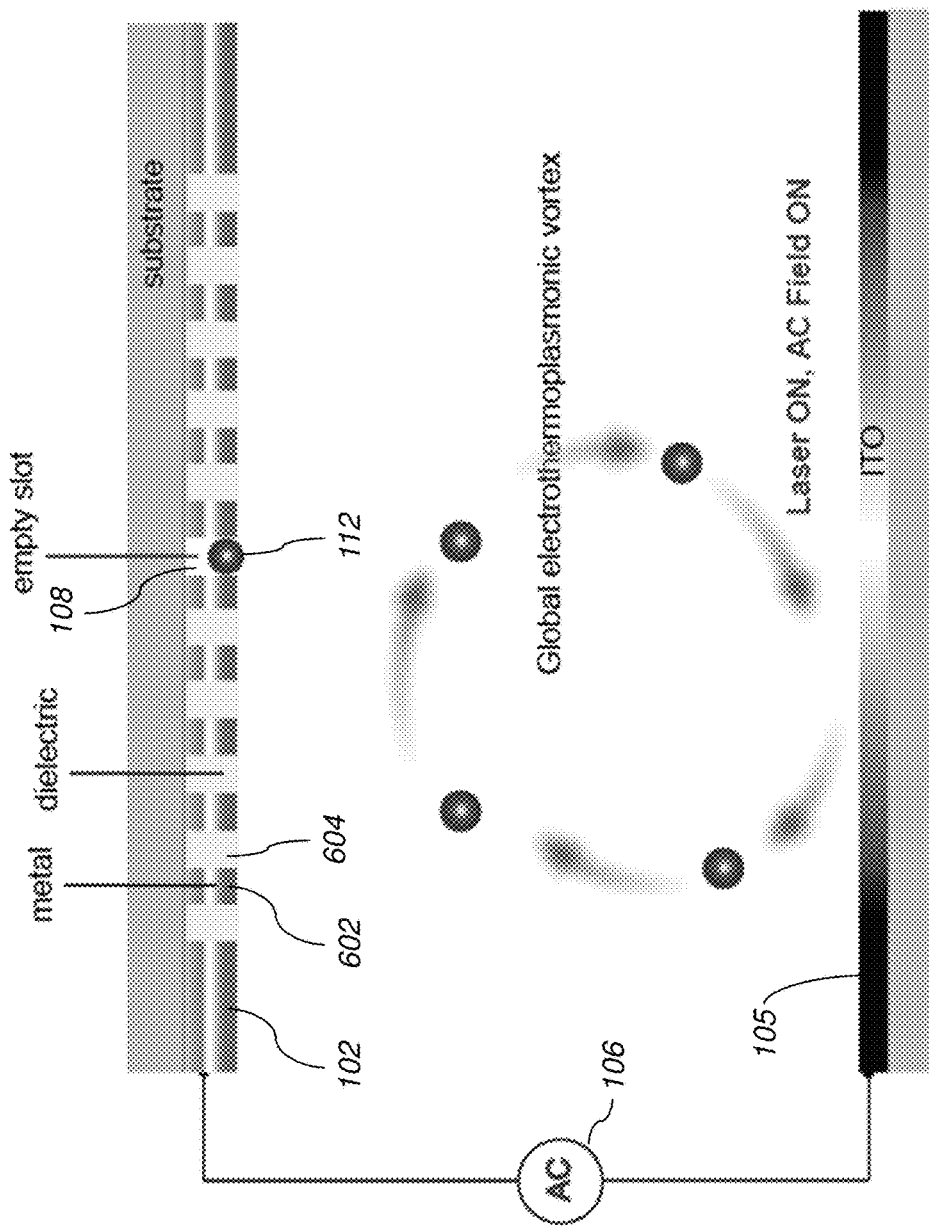
FIG. 7 is a diagram showing an embodiment having a film comprising alternating layers of metal dielectric composites.

FIG. 6 is a diagram showing a further embodiment, wherein the aperture film 102 is replaced with alternating horizontal layers of subwavelength metal nanostructures 602 and subwavelength dielectric nanostructures 604. These alternating layers of metal (602) and dielectric (604) subwavelength nanostructures serve as an indefinite medium and provides an optical cavity to confine the optical field to the deeply subwavelength scale and generate very strong optical gradient forces to trap the nanoparticles in the nanopore formed within the cavity. As shown in FIG. 7, the alternating metal nanostructures 602 and dielectric nanostructures 604 may be arranged as vertical portions, each extending through the thickness of the aperture layer 102. The alternating arrangement of FIGS. 6 and 7 increases the allowable range of nanopore diameters which may be used (for example, due to manufacturing differences), without causing a decrease in the attraction force of particles to the nanopores. Essentially, the arrangement provides flexibility such that nanopores with different sizes can resonate at the same frequency.

Figure 8:
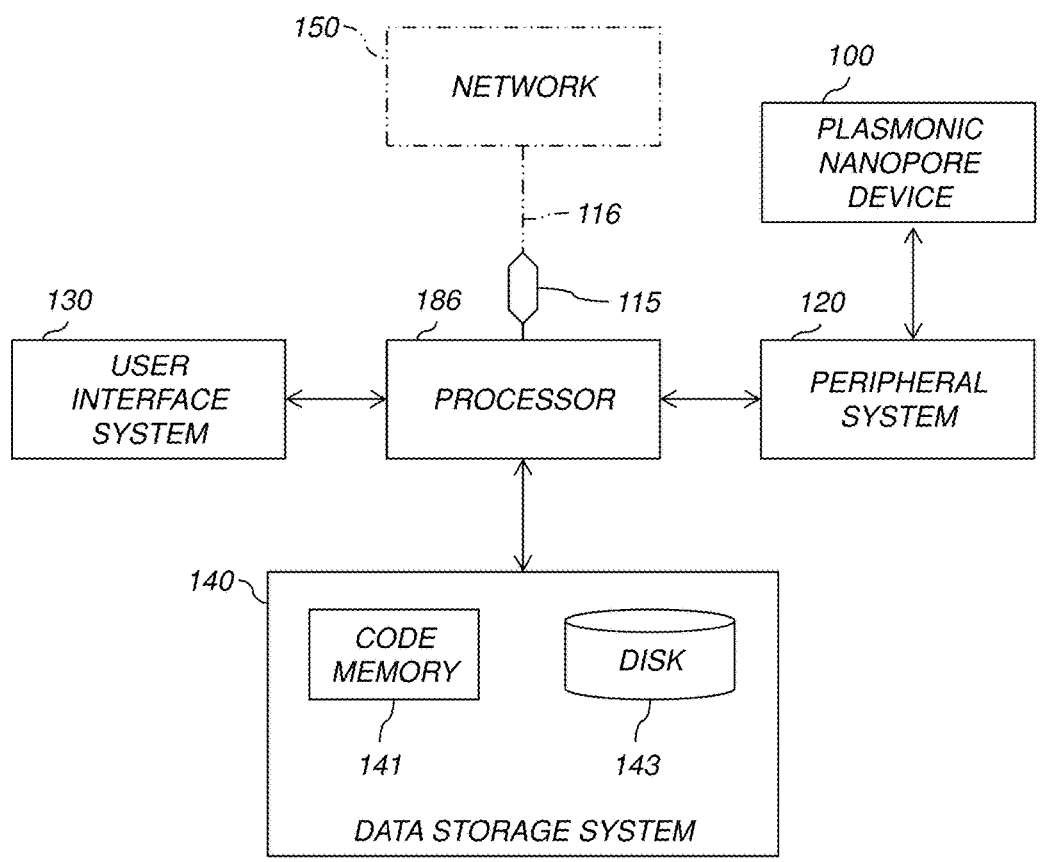
FIG. 8 is a diagram showing an example control system for interfacing with and controlling the apparatus of FIG. 1.

FIG. 8 is a high-level diagram showing the components of an exemplary data-processing system for controlling the apparatus 100 and analyzing data and performing other analyses described herein, and related components. The system includes a processor 186, a peripheral system 120, a user interface system 130, and a data storage system 140. The peripheral system 120, the user interface system 130 and the data storage system 140 are communicatively connected to the processor 186. Processor 186 can be communicatively connected to network 150 (shown in phantom), e.g., the Internet or a leased line, as discussed below. It shall be understood that the system 120 may include multiple processors 186 and other components shown in FIG. 6. The apparatus 100 (including light source 110 and electric field source 106 may optionally be controlled and/or communicated with using network 150 (from one or more data sources), peripheral system 120 and/or displayed using display units (included in user interface system 130) which can each include one or more of systems 186, 120, 130, 140, and can each connect to one or more network(s) 150. Processor 186, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Processor 186 can implement processes of various aspects described herein. Processor 186 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise. Processor 186 can include Harvard-architecture components, modified-Harvard-architecture components, or Von-Neumann-architecture components.

The phrase "communicatively connected" includes any type of connection, wired or wireless, for communicating data between devices or processors. These devices or processors can be located in physical proximity or not. For example, subsystems such as peripheral system 120, user interface system 130, and data storage system 140 are shown separately from the data processing system 186 but can be stored completely or partially within the data processing system 186.

The peripheral system 120 can include one or more devices configured to control the light source 110 and the electric field source 106. The peripheral system 120 can also include one or more devices to provide digital content records to the processor 186 to observe the result of the operations of the apparatus 100. For example, the peripheral system 120 can include digital still cameras, digital video cameras, cellular phones, or other data processors. The processor 186, upon receipt of digital content records from a device in the peripheral system 120, can store such digital content records in the data storage system 140.

The user interface system 130 can include a mouse, a keyboard, another computer (connected, e.g., via a network or a null-modem cable), or any device or combination of devices from which data is input to the processor 186. The user interface system 130 also can include a display device, a processor-accessible memory, or any device or combination of devices to which data is output by the processor 186. The user interface system 130 and the data storage system 140 can share a processor-accessible memory.

In various aspects, processor 186 includes or is connected to communication interface 115 that is coupled via network link 116 (shown in phantom) to network 150. For example, communication interface 115 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WiFi or GSM. Communication interface 115 sends and receives electrical, electromagnetic or optical signals that carry digital or analog data streams representing various types of information across network link 116 to network 150. Network link 116 can be connected to network 150 via a switch, gateway, hub, router, or other networking device.

Processor 186 can send messages and receive data, including program code, through network 150, network link 116 and communication interface 115. For example, a server can store requested code for an application program (e.g., a JAVA applet) on a tangible non-volatile computer-readable storage medium to which it is connected. The server can retrieve the code from the medium and transmit it through network 150 to communication interface 115. The received code can be executed by processor 186 as it is received, or stored in data storage system 140 for later execution.

Data storage system 140 can include or be communicatively connected with one or more processor-accessible memories configured to store information. The memories can be, e.g., within a chassis or as parts of a distributed system. The phrase "processor-accessible memory" is intended to include any data storage device to or from which processor 186 can transfer data (using appropriate components of peripheral system 120), whether volatile or non-volatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 140 can be a tangible non-transitory computer-readable storage medium, i.e., a non-transitory device or article of manufacture that participates in storing instructions that can be provided to processor 186 for execution.

In an example, data storage system 140 includes code memory 141, e.g., a RAM, and disk 143, e.g., a tangible computer-readable rotational storage device such as a hard drive. Computer program instructions are read into code memory 141 from disk 143. Processor 186 then executes one or more sequences of the computer program instructions loaded into code memory 141, as a result performing process steps described herein. In this way, processor 186 carries out a computer implemented process. For example, steps of methods described herein, blocks of the flowchart illustrations or block diagrams herein, and combinations of those, can be implemented by computer program instructions. Code memory 141 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into processor 186 (and possibly also other processors), to cause functions, acts, or operational steps of various aspects herein to be performed by the processor 186 (or other processor). Computer program code for carrying out operations for various aspects described herein may be written in any combination of one or more programming language(s), and can be loaded from disk 143 into code memory 141 for execution. The program code may execute, e.g., entirely on processor 186, partly on processor 186 and partly on a remote computer connected to network 150, or entirely on the remote computer.

The invention is inclusive of combinations of the aspects described herein. References to "a particular aspect" and the like refer to features that are present in at least one aspect of the invention. Separate references to "an aspect" (or "embodiment") or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

The invention claimed is:

1. An apparatus, comprising:
    a conductive transparent layer;
    a conductive film aperture layer mounted to a substrate, the aperture layer comprising a plurality of nanopores for trapping nanoparticles contained in a fluid situated between the transparent layer and the aperture layer;
    an electric field source connected between the transparent layer and the aperture layer.

2. The apparatus of claim 1, further comprising a light source configured to illuminate the nanopores to induce a flow of the nanoparticles towards the nanopores.

3. The apparatus of claim 2, wherein the light source is a laser.

4. The apparatus of claim 1, wherein the conductive transparent layer comprises indium tin oxide.

5. The apparatus of claim 1, further comprising a metasurface lens which focuses the light source onto the nanopores.

6. The apparatus of claim 5, wherein the diffraction grating is formed in the transparent layer.

7. The apparatus of claim 1, wherein the aperture layer comprises gold.

8. The apparatus of claim 1, wherein the electric field source comprises an alternating current source.

9. The apparatus of claim 8, wherein a frequency of the alternating current source is in the range of 5 KHz-100 KHz.

10. The apparatus of claim 1, wherein the field produced by the electric field generator is in the range of 40K-1M volts per meter.

11. The apparatus of claim 1, further comprising a random array of nanopores in the aperture layer separated from each other, wherein the random array absorbs broadband light by coupling of the nanopores to light to generate surface plasmons.

12. The apparatus of claim 1, wherein the nanopore is surrounded by a bullseye grating to provide concentration of light to the nanopore and outcoupling of light from the nanopore to free space.

13. The apparatus of claim 1, wherein the aperture layer comprises alternating layers of subwavelength metal and dielectric nanostructures.

14. The apparatus of claim 1, wherein the aperture layer comprises alternating portions of subwavelength metal and dielectric nano structures arranged configuration, each of said portions extending through the aperture layer thickness.

15. The apparatus of claim 1, wherein the nanopores have a diameter preferably in the range of 2 nm to 900 nm.

* * * * *